US009326753B2

(12) United States Patent
Nishimura

(10) Patent No.: US 9,326,753 B2
(45) Date of Patent: *May 3, 2016

(54) ULTRASONOGRAPH

(71) Applicant: KONICA MINOLTA, INC., Tokyo (JP)

(72) Inventor: Yushi Nishimura, Toon (JP)

(73) Assignee: KONICA MINOLTA, INC., Tokyo (JP)

( * ) Notice: Subject to any disclaimer, the term of this patent is extended or adjusted under 35 U.S.C. 154(b) by 249 days.

This patent is subject to a terminal disclaimer.

(21) Appl. No.: 13/939,877

(22) Filed: Jul. 11, 2013

(65) Prior Publication Data
US 2014/0163381 A1    Jun. 12, 2014

Related U.S. Application Data

(63) Continuation of application No. 12/676,484, filed as application No. PCT/JP2008/002438 on Sep. 4, 2008, now Pat. No. 8,506,489.

(51) Int. Cl.
A61B 8/00    (2006.01)
A61B 8/08    (2006.01)
A61B 8/06    (2006.01)
A61B 5/024   (2006.01)
A61B 5/0456  (2006.01)
A61B 5/00    (2006.01)

(52) U.S. Cl.
CPC ............... *A61B 8/5292* (2013.01); *A61B 8/06* (2013.01); *A61B 8/488* (2013.01); *A61B 5/024* (2013.01); *A61B 5/0456* (2013.01); *A61B 5/7257* (2013.01); *A61B 8/543* (2013.01)

(58) Field of Classification Search
CPC ............ A61B 8/00; A61B 8/488; A61B 8/06; A61B 8/5292
USPC ........................................................ 600/454
See application file for complete search history.

(56) References Cited

U.S. PATENT DOCUMENTS 5,033,472 A   7/1991   Sato et al.
5,375,599 A   12/1994  Shimizu
5,529,073 A   6/1996   Kielbasiewicz
5,657,760 A   8/1997   Ying et al.
(Continued)

FOREIGN PATENT DOCUMENTS

DE   101 18 180   5/2002
JP   8-173426     7/1996
(Continued)

Primary Examiner — Joel F Brutus
(74) Attorney, Agent, or Firm — Lucas & Mercanti, LLP

(57) ABSTRACT

An ultrasonograph that can automatically optimize the sweep rate of Doppler images and M-mode images according to the heart rate of a test subject. The ultrasonograph includes means for sending an ultrasonic beam into body tissue, a means for receiving an ultrasonic signal reflected off the body tissue and a blood flow, a means for constructing a cross-sectional image of the body tissue from the received signal, a means for performing phase detection on an ultrasonic Doppler blood flow signal, a means for calculating a frequency component of the Doppler blood flow signal, and a means for performing a sweeping display of the calculated frequency component as Doppler images in a time series. The ultrasonograph has a heart rate measuring means, an optimum sweep rate calculating means and an optimum sweep rate setting means.

7 Claims, 4 Drawing Sheets

(56) References Cited

U.S. PATENT DOCUMENTS

| | | |
|---|---|---|
| 6,525,525 B1 | 2/2003 | Azinger |
| 2002/0173721 A1 | 11/2002 | Grunwald et al. |
| 2003/0013959 A1* | 1/2003 | Grunwald et al. ............ 600/437 |
| 2003/0125624 A1 | 7/2003 | Shiki |
| 2003/0158484 A1 | 8/2003 | Pan et al. |
| 2004/0059220 A1 | 3/2004 | Mourad et al. |
| 2004/0186388 A1 | 9/2004 | Gerasimov |
| 2006/0079778 A1 | 4/2006 | Mo et al. |
| 2006/0084873 A1 | 4/2006 | Baba et al. |
| 2007/0016046 A1 | 1/2007 | Mozayeni et al. |
| 2007/0038086 A1 | 2/2007 | Ohtsuka |
| 2007/0167766 A1 | 7/2007 | Takimoto et al. |

FOREIGN PATENT DOCUMENTS

| | | |
|---|---|---|
| JP | 8-308843 | 11/1996 |
| JP | 2003-061958 | 3/2003 |
| JP | 2003-245279 | 9/2003 |
| JP | 3698173 | 7/2005 |
| JP | 2007-175069 | 7/2007 |

* cited by examiner

ULTRASONOGRAPH

TECHNICAL FIELD

The present invention relates to an ultrasonograph that measures a blood flow signal in a test subject with use of an ultrasonic Doppler effect, and in particular to technology for automatic optimization in the display of Doppler images and M-mode images in the device.

BACKGROUND ART

Ultrasonographs that obtain in real-time a blood flow signal in a test subject with use of an ultrasonic beam emitted from an ultrasonic probe conventionally have been used. With such ultrasonographs, depending on the frequency of the detected signal, there are cases in which aliasing occurs in an obtained Doppler image, and when such Doppler image aliasing occurs, it is necessary for an operator to adjust the pulse repetition frequency according to the blood flow velocity.

In view of this, in order to not force the operator to perform such a troublesome operation, there is known technology in which by detecting a signal existence region corresponding to a detectable frequency range, the repetition frequency (PRF) of ultrasonic beam transmission/reception and a baseline position (0 Hz position) are adjusted automatically so that the Doppler image does not cause aliasing to occur (e.g., see Patent Document 1).

In this technology disclosed in Patent Document 1, first an operation for classifying a Doppler spectrum obtained by FFT into a "value 0" portion and a "value 1" portion with use of a threshold value is performed on a certain range of a Doppler image. Next, a signal existence ratio, that is to say, a percentage occupied by the signal existence region, is obtained, and the PRF is set such that the signal existence ratio is approximately 0.6 to 0.8. Then, a signal existence region is obtained with respect to a Doppler spectrum obtained with use of the set PRF by performing a similar operation, and the baseline position is moved such that the center of the region in which the signal does not exist moves towards the edges of the screen.

On the other hand, technology also has been proposed in which, in the case in which the intensity of the blood flow signal changes, such as the case in which an ultrasonic contrast agent is used in blood flow measurement, in order to optimize the intensity of the obtained blood flow signal, the level of a signal retrieved from a Doppler signal detection unit is detected, and the gain of the signal is automatically adjusted (e.g., see Patent Document 2).

In this technology disclosed in Patent Document 2, an appropriate gain value that is in accordance with the signal level of the Doppler blood flow signal is determined with use of a table stored in a storing means such as a ROM in advance, thus automatically optimizing the gain, which is the luminance signal of the obtained Doppler image.

Patent Document 1: JP H08-308843A
Patent Document 2: JP H08-173426A

DISCLOSURE OF INVENTION

Problem to be Solved by the Invention

Regarding automation technology related to these conventional ultrasonographs, the technology disclosed in Patent Document 1 is for optimization with respect to the flow rate axis in a Doppler image, that is to say, the signal in the direction normally shown as the vertical axis in a Doppler image, whereas the technology disclosed in Patent Document 2 is for optimization with respect to the axis that corresponds to the Z axis in a Doppler image and that is in a direction perpendicular to the Doppler image plane. However, even if either one of such conventional technology is used, or both are used at the same time, it is not possible to optimize a Doppler image with respect to the time axis, that is to say, the direction of the horizontal axis in a Doppler image (i.e., it is not possible to set a flow rate desired by the operator).

Here, regarding the sweep rate of Doppler images obtained from a Doppler signal, in the case of displaying Doppler images of a test subject whose heart rate is, for example, 40 beats per minute, if the sweep rate of the Doppler images is two seconds per screen, it is only possible to display images representing approximately 1.3 heart beats in one screen. This creates a situation in which viewing and making determinations is difficult for the operator, and it is difficult to say that this is an optimized situation, that is to say, a situation in which the sweep rate desired by the operator has been set. If there is a desire to display images representing even more heart beats on the screen, it is necessary to perform optimization by reducing the sweep rate and lengthening the display time per screen to, for example, approximately four seconds.

In this way, the optimum sweep rate (the sweep rate desired by the operator) of Doppler images depends on the heart rate of the test subject, and since of course the heart rate varies greatly depending on the subject and the state of the subject at the time of measurement, the operator has needed to set, on a case-by-case basis, the optimum sweep rate for each test subject while viewing the Doppler images.

The present invention has been achieved in order to solve such conventional problems, and an object thereof is to provide an ultrasonograph that automatically can optimize the sweep rate (set the sweep rate to a rate desired by an operator) of Doppler images and M-mode images according to the heart rate of a test subject, without requiring the operator to perform a troublesome operation.

Means for Solving Problem

In order to solve the above issues, an ultrasonograph of the present invention is an ultrasonograph provided with a means for sending an ultrasonic beam into body tissue, a means for receiving an ultrasonic signal that has been reflected off the body tissue and a blood flow, a means for constructing a cross-sectional image of the body tissue from the received ultrasonic signal, a means for performing phase detection on an ultrasonic Doppler blood flow signal that has been reflected off the body tissue by the blood flow, a means for calculating a frequency component of the Doppler blood flow signal on which phase detection has been performed, and a means for performing a sweeping display of the calculated frequency component as Doppler images in a time series. The ultrasonograph has a heart rate measuring means for measuring a heart rate of a test subject at a predetermining timing, and the ultrasonograph includes; an optimum sweep rate calculating means for calculating an optimum sweep rate based on the heart rate obtained by the heart rate measuring means; and an optimum sweep rate setting means for setting a sweep rate of at least either of the Doppler images and M-mode images.

According to this configuration, with the ultrasonograph according to the present invention, an operator can obtain Doppler images and M-mode images at a desired optimum sweep rate without performing a troublesome operation.

Also, the ultrasonograph according to the present invention may further may include: a means for acquiring an electrocardiographic waveform of the test subject; and an R wave detecting means for detecting an R wave from the acquired electrocardiographic waveform, wherein the heart rate measuring means may have a calculating means for calculating a heart rate per unit time based on a time interval of the R wave obtained by the R wave detecting means.

According to this configuration, it is possible to measure the heart rate to be the reference for calculating the optimum sweep rate, using the R-wave obtained from the electrocardiographic waveform, and without use of Doppler images.

Also, the ultrasonograph according to the present invention further may include: a Doppler tracing means for tracing each maximum flow velocity point in the Doppler images, wherein the heart rate measuring means may have an estimating means for estimating a time required for each heart beat from a Doppler trace waveform obtained by the Doppler tracing means, and a calculating means for calculating a heart rate per unit time based on the time required for each heart beat obtained by the estimating means.

According to this configuration, it is possible to measure the heart rate to be the reference for calculating the optimum sweep rate, using only Doppler images, and without use of an ECG waveform.

Furthermore, in the ultrasonograph according to the present invention, it is preferable that the optimum sweep rate setting means is realized by a user interface that can be operated by an operator, and the sweep rate of at least either of the Doppler images and the M-mode images is optimized due to the operator operating the user interface.

According to this configuration, the operator can obtain Doppler images and M-mode images at a desired optimum sweep rate by operating the user interface.

Moreover, in the ultrasonograph according to the present invention, it is preferable that the optimum sweep rate setting means automatically executes the optimum sweep rate setting in a case in which a mode including a display of at least either of the Doppler images and the M-mode images has been transitioned to.

According to this configuration, it is possible automatically to obtain Doppler images and M-mode images having the optimum sweep rate at the time of mode transition.

Also, in the ultrasonograph according to the present invention, the optimum sweep rate setting means may be a means enabling the operator to set in advance how many heart beats are represented by at least either of the Doppler images and the M-mode images displayed in one screen.

According to this configuration, the operator intentionally can set how many heart beats are represented by the Doppler images or M-mode images displayed in one screen.

Moreover, the ultrasonograph according to the present invention may include a recording means for recording the Doppler blood flow signal, and after at least either of the Doppler images and the M-mode images have been frozen, the heart rate measuring means may obtain a heart rate with use of data recorded by the recording means, and the sweep rate of at least either of the Doppler images and the M-mode images may be set.

According to this configuration, it is possible to optimize the sweep rate of Doppler images even after the Doppler images or the M-mode images have been frozen.

Effects of the Invention

An ultrasonograph of the present invention constantly can obtain optimum Doppler images by automatically optimizing the sweep rate of Doppler images based on the detected heart rate of a test subject, without an operator performing a troublesome operation.

Figure 1:
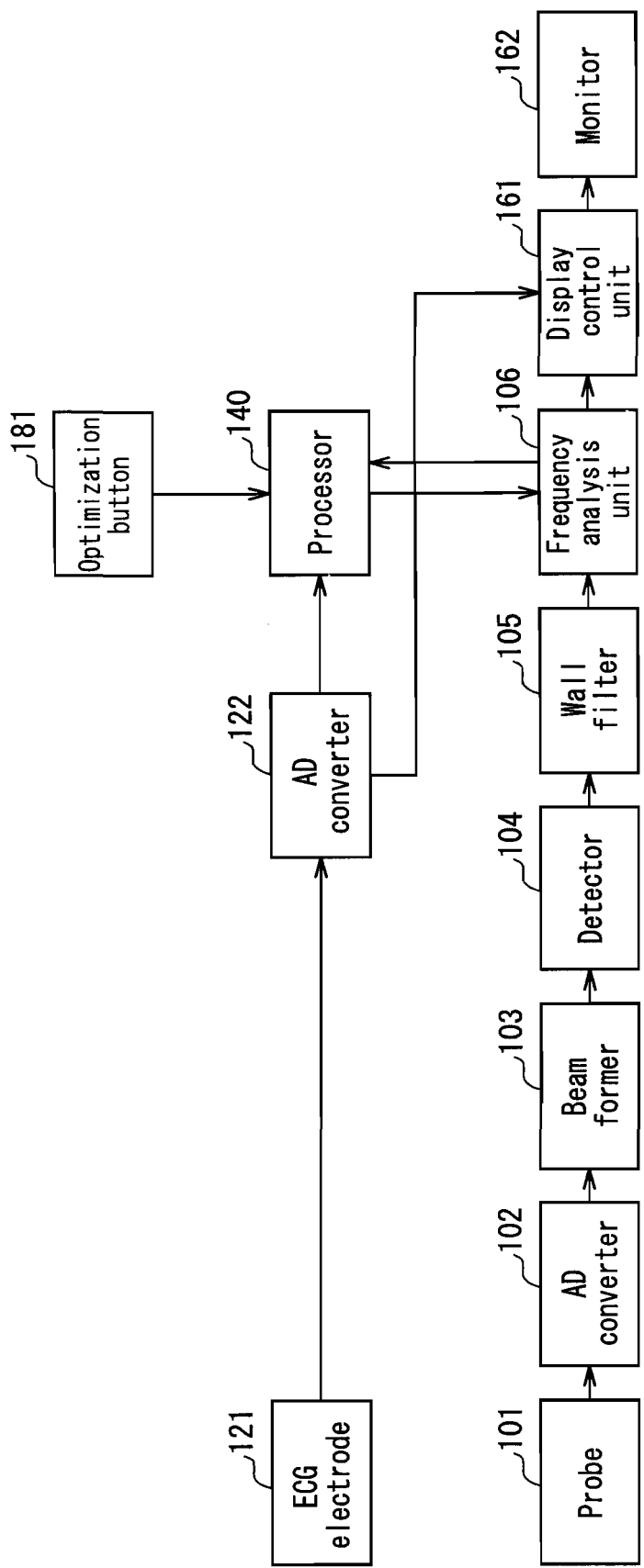
FIG. 1 is a block diagram showing relevant portions of an exemplary configuration of an ultrasonograph according to Embodiment 1 of the present invention.

REFERENCE SIGNS LIST 101 probe
102 AD converter
103 beam former
104 detector
105 wall filter
106 frequency analysis unit
121 ECG electrode
122 AD converter
140 processor
141 R-wave detection unit
142 Doppler trace calculation unit
143 heart rate measurement unit
144 sweep rate calculation unit
145 sweep rate control unit
161 display control unit
162 monitor
181 optimization button
301 data memory
302 data memory
303 scene memory

DESCRIPTION OF THE INVENTION

The following describes embodiments of the present invention with reference to the drawings.

Embodiment 1

FIG. 1 is a block diagram showing relevant portions of an exemplary configuration of an ultrasonograph according to Embodiment 1 of the present invention.

FIG. 1 shows in particular portions of the ultrasonograph according to the present invention that are for obtaining an ultrasonic Doppler signal through displaying it as a Doppler image. Accordingly, a pulse generation circuit or pulsar, which are means for sending an ultrasonic beam into body tissue, and a means for constructing a cross-sectional image of body tissue from an ultrasonic signal that has been reflected off the body tissue, have the same configurations as those in a normal ultrasonograph, and depictions thereof have been omitted.

A probe 101 is a means for receiving an ultrasonic Doppler signal, an AD converter 102 receives the ultrasonic Doppler signal and converts it into a digital signal, a beam former 103 performs delay and synthesis on the AD converted ultrasonic reception signal, a detector 104 is a means for detecting a Doppler shift component, that is to say, a Doppler signal phase, from the delayed and synthesized ultrasonic signal, a wall filter 105 eliminates a wall component in the Doppler signal, and a frequency analysis unit 106 is a means for performing frequency analysis on the received signal and calculating a frequency component of a Doppler blood flow signal.

Also, an ECG electrode 121 is a means for acquiring an electrocardiogram waveform (ECG waveform) of a living organism that is the test subject, and an AD converter 122 converts the acquired ECG waveform into a digital signal. A processor 140 receives a command from a user and determines an optimum sweep rate for Doppler images. A display control unit 161 is a means for performing a sweeping display of the frequency component obtained by the frequency analysis unit 106 and the ECG signal obtained from the AD converter 122, as Doppler images and ECG images respectively in a time series. A monitor 162 displays the Doppler images and ECG images, and an optimization button 181 is for being operated by an operator in order to optimize the sweep rate of the Doppler images.

The ultrasonic beam sent by the probe 101 is reflected within the living organism that is the test subject, received by the probe 101, and converted into a digital signal by the AD converter 102. Then, the digital signal is delayed and synthesized by the beam former 103, and then input to the detector 104.

The detector 104 demultiplexes the Doppler signal using a method known as quadrature detection. The wall filter 105 is a high pass filter, and the wall filter 105 eliminates low frequency noise (walls) that is generated by body movement of the test subject and movement of the walls of biological organs. At a timing notified by the processor 140, the frequency analysis unit 106 calculates frequency components from the output signal of the wall filter 105 using Fast Fourier Transformation (FFT), converts the frequency components to luminance values, and outputs the luminance values to the display control unit 161 as a Doppler image.

Meanwhile, an output signal from the ECG electrode 121, which has been mounted so as to be in contact with the body surface of the test subject, is converted into a digital signal by the AD converter 122, and output to the display control unit 161. The display control unit 161 synthesizes the Doppler image that has been input from the frequency analysis unit 106 and the ECG signal that has been input from the AD converter 122 in the same time phase, and outputs the synthesized Doppler image and ECG signal to the monitor 162. The monitor 162 performs a sweeping display of the Doppler image and the ECG signal that have input thereto.

Here, the processor 140 internally includes a heart rate measurement unit 143, which is a calculating means for calculating a heart rate, and each time the operator depresses an optimization button 181 (e.g., a button provided on the console of the ultrasonograph) as a user interface at a predetermined timing, the heart rate is measured by the processor 140, or more specifically the heart rate measurement unit 143, and the sweep rate of the Doppler images is optimized (set to the rate desired by the operator). In other words, due to the depression of the optimization button 181, the processor 140 measures the optimum sweep rate for the Doppler images, and instructs the frequency analysis unit 106 regarding an FFT execution timing in order to realize the calculated optimum sweep rate.

Figure 2:
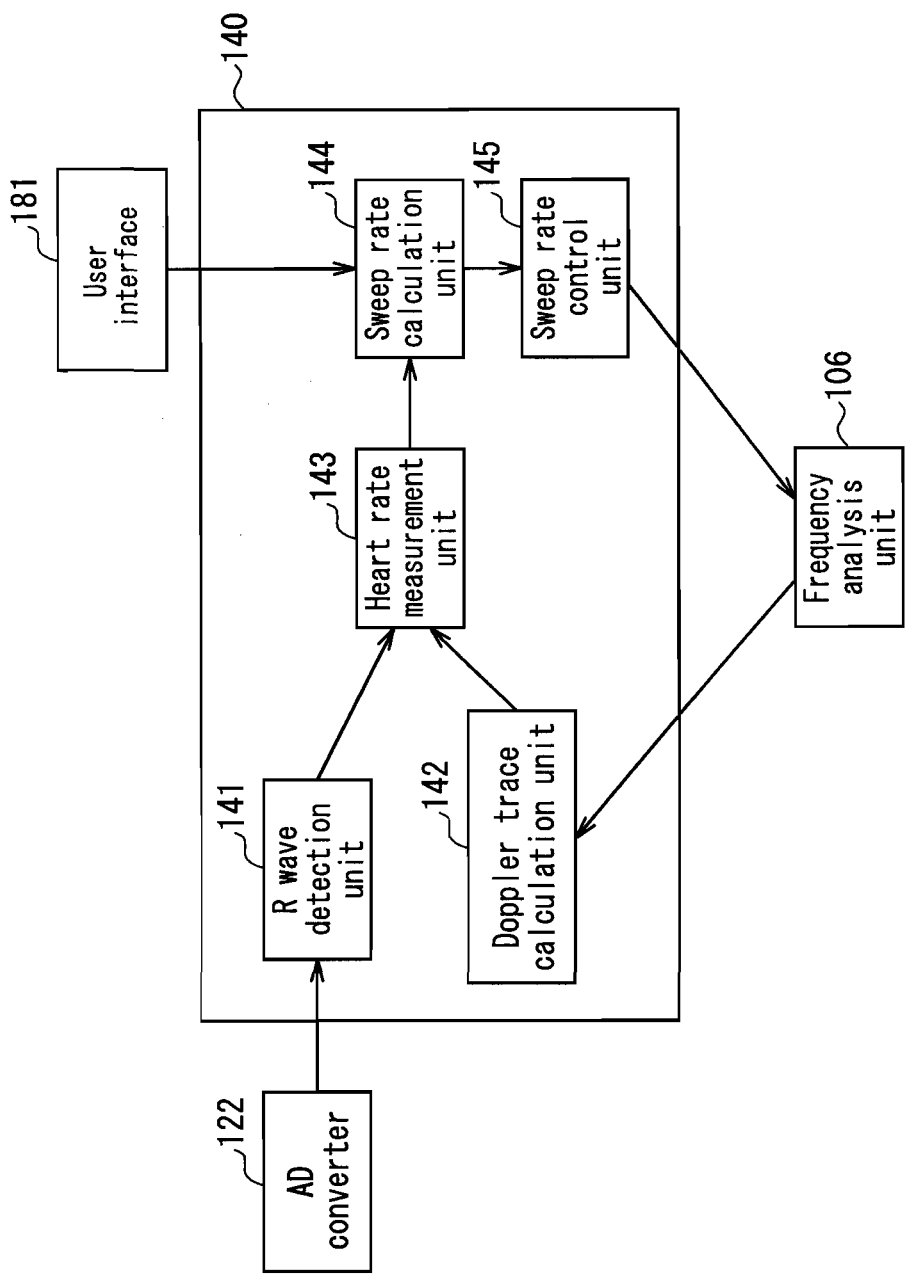
FIG. 2 is a block diagram showing a configuration of a processor of the ultrasonograph according to Embodiment 1 of the present invention.

The following describes in detail the configuration of the processor with reference to FIG. 2. FIG. 2 is a block diagram showing the configuration of the processor 140.

An R-wave detection unit 141, which is an R-wave detecting means, analyzes the ECG waveform that has been input by the AD converter 122, detects an R-wave in the waveform, and notifies the detection time to the heart rate measurement unit 143, which is the calculating means for calculating a heart rate.

Then, in the ultrasonograph according to the present embodiment, in the case of calculating a heart rate per unit time based on the time interval of the R-wave, the heart rate that has been calculated based on the notified detection time is used as the heart rate of the test subject that is to be the reference for setting the sweep rate of the Doppler images.

Meanwhile, a Doppler trace calculation unit 142, which is a Doppler tracing means and also an estimating means, analyzes the frequency component data of the Doppler signal that has been obtained by the frequency analysis unit 106, and estimates maximum flow velocity points. By connecting, that is to say, tracing the estimated maximum flow velocity points in a time series, the Doppler trace calculation unit 142 generates a waveform generally known as a so-called Doppler trace waveform, and outputs the waveform to the heart rate measurement unit 143, which is the calculating means.

Then, in the ultrasonograph according to the present embodiment, in the case of estimating and calculating the time required for each heart beat from the Doppler trace waveform, the heart rate that has been calculated based on the notified detection time is used as the heart rate of the test subject that is to be the reference for setting the sweep rate of the Doppler images.

The heart rate measurement unit 143, which is the heart rate measuring means, calculates a heart rate per unit time of the test subject with use of either the R-wave detection time obtained by the R-wave detection unit 141 or the Doppler trace waveform obtained by the Doppler trace calculation unit 142, and notifies the obtained heart rate to a sweep rate calculation unit 144, which is an optimum sweep rate calculating means.

Note that the operator presets whether the R-wave detection time or the Doppler trace waveform is to be used in order to calculate the heart rate. Also, the operator sets in the processor 140, in advance, how many heart beats are represented by Doppler images displayed in one screen of the monitor 162.

The sweep rate calculation unit 144 determines the FFT execution cycle of the frequency analysis unit 106 through the expression (N×T)/W, where N is the heart rate to be displayed in one screen that has been set in advance by the operator (the heart rate that is desired by the operator and is to be displayed in one screen according to the sweep rate), W is the width of one screen (number of dots), and T is the time required for one heart beat measured by the heart rate measurement unit 143.

A sweep rate control unit 145, which is an optimum sweet rate setting means, instructs the frequency analysis unit 106 to execute the FFT at the FFT execution cycle calculated by the sweep rate calculation unit 144.

For example, in the case in which the heart rate to be displayed in one screen is two heart beats, the width of one screen is 500 dots, and the time required for one heart beat is one second, the frequency analysis unit 106 executes the FFT at a cycle of 4 ms.

Note that in the ultrasonograph according to the present embodiment, a Doppler image generated by one instance of the FFT is rendered on a one-dot vertical line in the screen of the monitor 162.

Also, with the ultrasonograph according to the present embodiment, the case has been described in which a button is provided as a means for sending a signal to the heart rate measurement unit 143 at a predetermined timing, and in order to optimize the sweep rate, first such button is depressed by the operator, but the present invention is not limited to this.

For example, a configuration is possible in which the optimum sweep rate is obtained in advance by the R-wave detection unit 141, the heart rate detection unit 143, and the sweep rate calculation unit 144 during a cross-sectional image display mode (B mode), and upon transitioning to the Doppler mode, the automatically obtained optimum sweep rate is realized. Also, as the predetermined timing, a signal may be sent to the heart rate measurement unit 143 if a mode-switching operation switch has been pressed, if a button for screen-switching has been pressed, at a time interval that has been set arbitrarily, or the like, and in such cases, it is not particularly necessary for the optimization button 181 to be provided.

Also, as described above, it is possible to additionally to enable the operator to set how many heart beats are represented by Doppler images displayed in one screen, and in this case, it is sufficient to provide an appropriately displayed heart rate setting means for notifying the processor of the operator's setting.

Note that such a displayed heart rate setting means is not essential in the present embodiment, and therefore does not necessarily need to be provided.

Also, although the heart rate calculating means for obtaining the optimum sweep rate is configured so as to be able to obtain the optimum sweep rate from both the R-wave detection time and the Doppler trace waveform in the present embodiment, it goes without saying that there is no problem with a configuration in which the optimum sweep rate is obtained from only one of these.

Embodiment 2

Next is a description of Embodiment 2 of the ultrasonograph according to the present invention with reference to the drawings.

Figure 3:
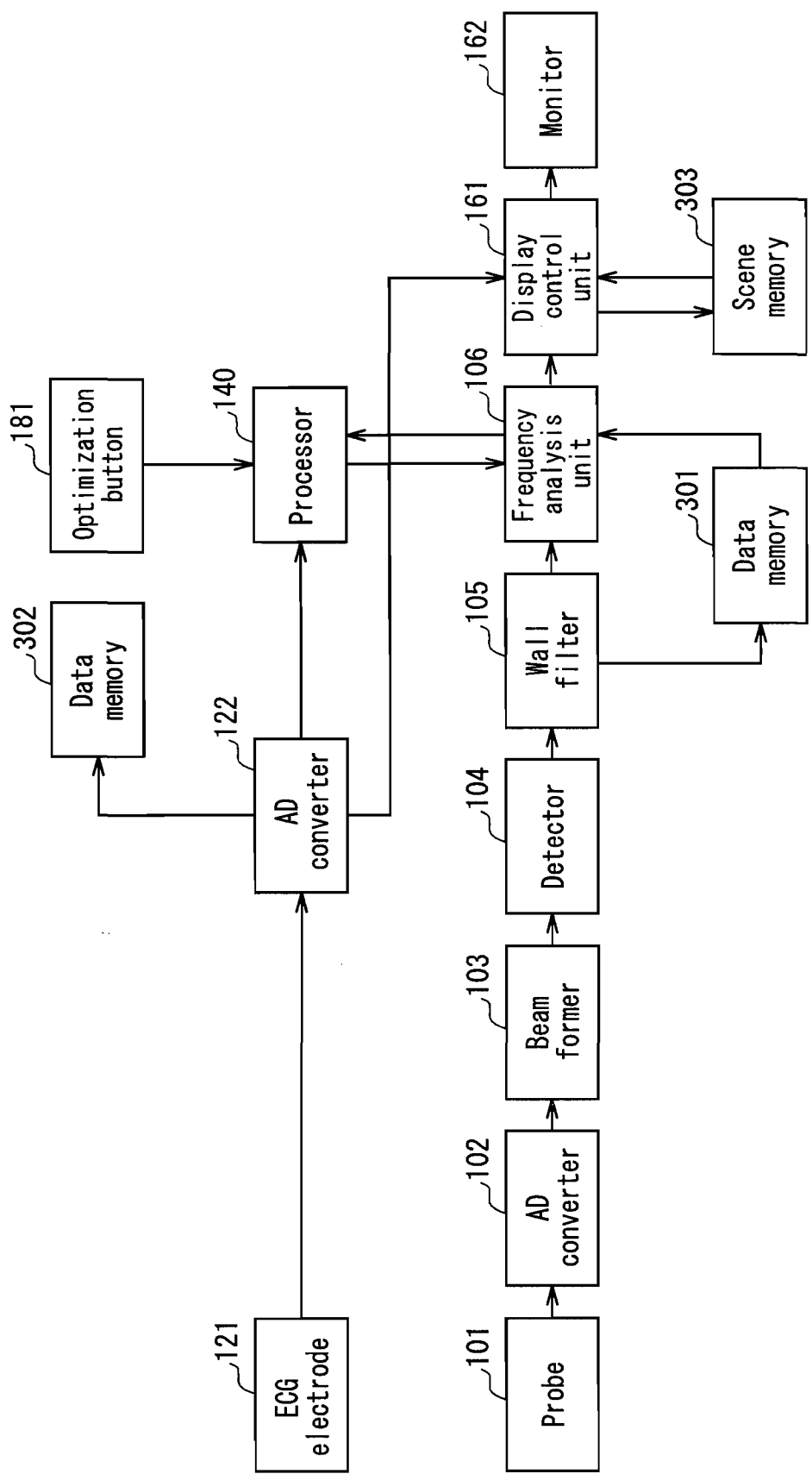
FIG. 3 is a block diagram showing relevant portions of an exemplary configuration of an ultrasonograph according to Embodiment 2 of the present invention.

FIG. 3 is a block diagram showing an exemplary configuration of relevant portions of the ultrasonograph according to Embodiment 2 of the present invention. Note that likewise with FIG. 1, FIG. 3 also shows only relevant constituent portions of the ultrasonograph according to the present invention. Also, the same reference numerals as in FIG. 1 have been given to portions that have the same configurations and functions as those described in Embodiment 1 with use of FIG. 1, and descriptions of such portions have been omitted.

The ultrasonograph according to Embodiment 2 of the present invention that is shown in FIG. 3 differs from Embodiment 1 shown in FIG. 1 with respect to having a data memory 301, which is a recording means for recording output data of the wall filter 105, a data memory 302 that records output data of the AD converter 122, and a scene memory 303 that records Doppler images and ECG images that have been converted to luminance information.

The following describes operations performed in the ultrasonograph according to the present embodiment.

With the ultrasonograph according to the present embodiment, in a live state before the Doppler images are frozen, the output signal of the wall filter 105 is stored in the data memory 301 along with the time at which processing was performed thereon, and the output data of the AD converter 122 is stored in the data memory 302 along with the time at which processing was performed thereon.

Then, if the operator has depressed the optimization button 181 after the Doppler images have been frozen, the frequency analysis unit 106 executes the FFT on the data in the data memory 301 at the FFT execution cycle that was set immediately before the freezing, and inputs this execution result to the Doppler trace calculation unit 142 in the processor 140. The FFT execution cycle at this time is determined not by the time when the FFT actually is performed, but rather by the time when the Doppler data pieces stored in the data memory 301 were processed.

The processor 140 reads the ECG data stored in the data memory 302, and inputs such ECG data to the R-wave detection unit 141. At this time, the detection time that the R-wave detection unit 141 notifies to the heart rate measurement unit 143 is based on the time, which is stored in the data memory 302, at which the AD converter 122 processed the ECG data.

With use of the data obtained from the frequency analysis unit 106 and the data memory 302, the processor 140 performs processing similar to that in Embodiment 1 of the present invention, thus determining the optimum sweep rate, that is to say, the FFT execution cycle. Here as well, the time at which the Doppler data pieces stored in the data memory 301 were processed is the time basis of the execution cycle.

The frequency analysis unit 106 executes the FFT on all the data in the data memory 301 at the FFT execution cycle instructed by the processor 140, converts the obtained frequency component data into luminance values, and inputs the luminance values to the display control unit 161 as a Doppler image.

Then, the display control unit 161 deletes the data in the scene memory 303, and stores therein the Doppler image that has been newly input.

Note that although the present embodiment describes the example in which the optimization of the sweep rate is performed due to the operator depressing the optimization button 181, the present invention is not limited to this, and as described in Embodiment 1, the optimization of the sweep rate may be performed upon transitioning to a mode including Doppler image display.

Also, although a configuration including the data memory 302 that stores the output data of the AD converter 122 has been described, the data memory 302 is unnecessary in the case in which only the Doppler trace waveform is used as the heart rate calculating means for obtaining the optimum sweep rate.

The above has described specific embodiment of the ultrasonograph according to the present invention, and the following describes operations of the ultrasonograph according to the present invention from the viewpoint of the operator.

If the operator has depressed the optimization button 181 after having frozen the Doppler images, the currently displayed Doppler images are deleted, and frozen Doppler images in which the scale in the time direction, that is to say, the horizontal axis direction has been optimized are newly displayed. For example, if the display width of the Doppler images from after optimization has been set in advance by the operator to be two heart beats in one screen, Doppler images representing two heart beats are displayed on the screen after the optimization button 181 has been depressed.

Note that an example of setting the sweep rate of the Doppler images has been given in the description of the above embodiments of the ultrasonograph of the present invention. However, in the ultrasonograph of the present invention, even with M-mode images, the sweep rate can be optimized by using a method of measuring the heart rate by calculating the R-wave.

Figure 4:
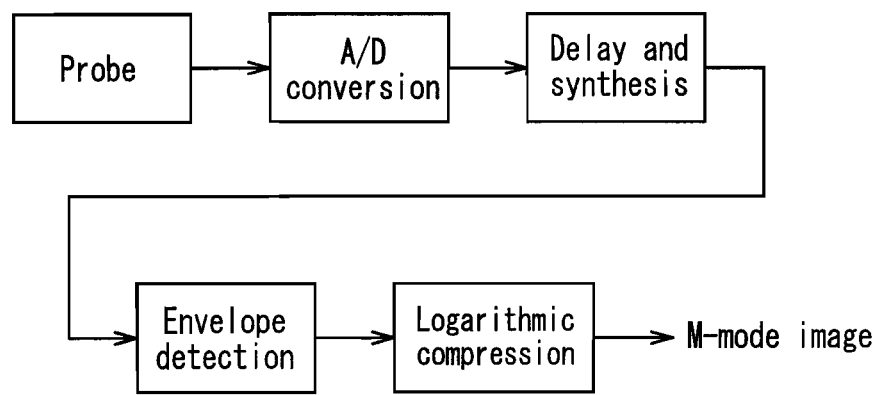
FIG. 4 is a diagram for describing the flow of signal processing for displaying an M-mode image.

FIG. 4 is a diagram showing an example of the flow of signal processing for obtaining an M-mode image.

As shown in FIG. 4, digital conversion is performed on an ultrasonic waveform obtained by the probe, delay and synthesis is then performed, and thereafter an envelope detecting means performs envelope detection in order to obtain a signal indicating biological information that has been superimposed on the transmission frequency. Thereafter, in order to obtain the luminance information, a means for constructing an M-mode image performs logarithmic compression, thus obtaining an M-mode image. Note that at the time of performing logarithmic compression after the envelope detection, gain adjustment for adjusting the luminance may be performed in order to facilitate viewing by the operator.

With the ultrasonograph according to the present invention, even in the case of displaying M-mode images obtained in this way, it is possible automatically to optimize the sweep rate likewise to the case of displaying Doppler images as described above in detail. Note that the various types of processing performed on the M-mode image signal in the ultrasonograph of the present embodiment can be various types of processing that are equivalent to the processing described in the above embodiment as being performed on the Doppler images.

INDUSTRIAL APPLICABILITY

An ultrasonograph according to the present invention can optimize the sweep rate of Doppler images and M-mode images based on a measured heart rate, and is useful in medical applications and the like.

The invention claimed is:

1. An ultrasonograph to send an ultrasonic beam into body tissue and acquiring an ultrasonic Doppler signal based on an ultrasonic signal reflected off the body tissue and a blood flow, comprising:
    an ultrasonic blood flow signal filtering unit that eliminates a low frequency component that is a part of the Doppler signal and that is generated by movement of the body tissue;
    a frequency analysis unit that calculates a frequency component of the ultrasonic Doppler signal from which the low frequency component has been eliminated by the ultrasonic blood flow signal filtering unit;
    a display control unit that performs in a time series a sweeping display of the frequency component as Doppler images calculated by the frequency analysis unit;
    a Doppler trace calculation unit that generates a Doppler trace waveform based on the frequency component calculated by the frequency analysis unit;
    a heart rate measurement unit that measures a heart rate of a test subject based on the Doppler trace waveform at a predetermined timing;
    a sweep rate calculation unit that calculates a sweep rate based on the heart rate obtained by the heart rate measurement unit; and
    a sweep rate control unit that sets the sweep rate of the Doppler images based on the sweep rate calculated by the sweep rate calculation unit.

2. The ultrasonograph according to claim 1, further comprising:
    an operation unit that can be operated by an operator,
    wherein the sweep rate control unit sets the sweep rate of the Doppler images based on an operation of the operator.

3. The ultrasonograph according to claim 2, wherein the operation unit is capable of setting how many heart beats are represented by the Doppler images in one screen.

4. The ultrasonograph according to claim 1, wherein the sweep rate control unit automatically executes a sweep rate setting in a case in which a mode including a display of the Doppler images has been transitioned to.

5. The ultrasonograph according to claim 1, wherein the heart rate measurement unit calculates a time required for each heart beat from the Doppler trace waveform obtained by the Doppler trace calculation unit, and calculates the heart rate based on a time required for each heart beat.

6. A processor of an ultrasonograph that performs a sweeping display of Doppler images in a time series based on a frequency component of an ultrasonic Doppler signal from which a low frequency component generated by movement of tissue has been eliminated, comprising:
    a Doppler trace calculation unit that generates a Doppler trace waveform based on the frequency component;
    a heart rate measurement unit that measures a heart rate of a test subject at a predetermined timing based on the Doppler trace waveform;
    a sweep rate calculation unit that calculates a sweep rate based on the heart rate obtained by the heart rate measurement unit; and
    a sweep rate control unit that sets a sweep rate of Doppler images for which the ultrasonograph performs a sweeping display based on a sweep rate calculated by the sweep rate calculation unit.

7. The processor according to claim 6, wherein the heart rate measurement unit calculates a time required for each heart beat from the Doppler trace waveform obtained by the Doppler trace calculation unit, and calculates the heart rate based on a time required for each heart beat.

* * * * *